US012303466B2

(12) United States Patent
Xu et al.

(10) Patent No.: US 12,303,466 B2
(45) Date of Patent: May 20, 2025

(54) DUODENUM BUILT-IN JEJUNUM CANNULA RELEASING SYSTEM AND A USE METHOD THEREFOR (71) Applicant: HANGZHOU TANGJI MEDICAL TECHNOLOGY CO., LTD, Hangzhou (CN)

(72) Inventors: Tianhong Xu, Hangzhou (CN); Yuxing Zuo, Hangzhou (CN); Jie Cao, Hangzhou (CN); Yan Lu, Hangzhou (CN); Xiaomin Yang, Hangzhou (CN)

(73) Assignee: HANGZHOU TANGJI MEDICAL TECHNOLOGY CO., LTD, Zhejiang (CN)

( * ) Notice: Subject to any disclaimer, the term of this patent is extended or adjusted under 35 U.S.C. 154(b) by 1281 days.

(21) Appl. No.: 16/981,896

(22) PCT Filed: Apr. 30, 2019

(86) PCT No.: PCT/CN2019/085229
§ 371 (c)(1),
(2) Date: Sep. 17, 2020

(87) PCT Pub. No.: WO2019/210856
PCT Pub. Date: Nov. 7, 2019

(65) Prior Publication Data
US 2021/0121369 A1 Apr. 29, 2021

(30) Foreign Application Priority Data
May 3, 2018 (CN) .................. 201810415050.4

(51) Int. Cl.
A61J 15/00 (2006.01)
A61F 2/04 (2013.01)
(Continued)

(52) U.S. Cl.
CPC ............. *A61J 15/0069* (2013.01); *A61F 2/04* (2013.01); *A61F 2/962* (2013.01); *A61F 2/966* (2013.01);
(Continued)

(58) Field of Classification Search
CPC ...... A61F 5/0089; A61F 2/962; A61F 5/0076; A61F 2002/9511
See application file for complete search history.

(56) References Cited

U.S. PATENT DOCUMENTS 5,246,445 A * 9/1993 Yachia .............. A61M 25/0017
606/104
8,801,647 B2 8/2014 Melanson et al.
(Continued)

FOREIGN PATENT DOCUMENTS

CN 202751415 U 2/2013
CN 107158546 A 9/2017
(Continued)

OTHER PUBLICATIONS

Office Action with regard to the counterpart CA Patent Application No. 3,094,114 mailed Nov. 5, 2021.
(Continued)

Primary Examiner — Rebecca S Preston
(74) Attorney, Agent, or Firm — BCF LLP (57) ABSTRACT A duodenum built-in jejunum cannula releasing system and a use method therefor, the system including: implanting device, pushing assembly, fixing line and releasing line. The implanting device includes storage pipe shell, releaser, membrane pipe and stent; the storage pipe shell is tubular and provided with near-end opening and far-end opening; the membrane pipe and the stent which are to be released are arranged in the storage pipe shell in folded state; the pushing assembly includes push-pull guiding wire, inner pipe,
(Continued)

middle pipe and outer pipe which are sleeved with one another from the inside out in sequence and may move relative to one another.

15 Claims, 7 Drawing Sheets

(51) Int. Cl.
  *A61F 2/962* (2013.01)
  *A61F 2/966* (2013.01)
  *A61F 5/00* (2006.01)
(52) U.S. Cl.
  CPC .......... *A61F 5/0036* (2013.01); *A61F 5/0089* (2013.01); *A61F 2002/045* (2013.01)

(56) References Cited

U.S. PATENT DOCUMENTS

| | | | |
|---|---|---|---|
| 2006/0004433 A1* | 1/2006 | Greenberg | A61F 2/95 623/1.11 |
| 2006/0009858 A1* | 1/2006 | Levine | A61F 5/0089 623/23.65 |
| 2006/0161265 A1 | 7/2006 | Levine et al. | |
| 2009/0171382 A1* | 7/2009 | Dillon | A61F 5/0036 606/192 |
| 2013/0030351 A1* | 1/2013 | Belhe | A61F 5/0079 604/9 |
| 2016/0095733 A1 | 4/2016 | Sharma et al. | |

FOREIGN PATENT DOCUMENTS

| | | |
|---|---|---|
| CN | 108464945 A | 8/2018 |
| RU | 2454974 C2 | 7/2012 |
| RU | 2651695 C2 | 4/2018 |
| WO | 2012087658 A1 | 6/2012 |
| WO | 2017132679 A1 | 8/2017 |

OTHER PUBLICATIONS

International Search Report (including English Translation) and Written Opinion with regard to PCT/CN2019/085229 mailed Jul. 17, 2019.
English Abstract for CN107158546 retrieved on Espacenet on Sep. 14, 2020.
English Abstract for CN108464945 retrieved on Espacenet on Sep. 14, 2020.
English Abstract for CN202751415 retrieved on Espacenet on Sep. 14, 2020.
Office Action with regard to the counterpart IN Patent Application No. 202027052474 dated Dec. 13, 2021.
European Search Report with regard to the counterpart EP Patent Application No. 19795911.7 completed May 12, 2021.
Decision to Grant and Search Report with regard to the counterpart RU Patent Application No. 2020132991 dated May 26, 2021, and Search Report completed Apr. 19, 2021.
Search Report with regard to the counterpart BR Patent Application No. 112020019784-0 completed Jan. 6, 2023.

* cited by examiner

DUODENUM BUILT-IN JEJUNUM CANNULA RELEASING SYSTEM AND A USE METHOD THEREFOR

CROSS-REFERENCE TO RELATED APPLICATIONS

The present application is a National Stage of International Application No. PCT/CN2019/085229, entitled "Duodenum built-in jejunum cannula releasing system and a use method therefor," filed on Apr. 30, 2019, which claims priority to Chinese Patent Application number 201810415050.4, filed on May 3, 2018, with the Chinese Patent Office, the contents of each of which are incorporated herein by reference in their entirety.

TECHNICAL FIELD

The present disclosure relates to the technical field of medical instruments, in particular to a jejunum cannula releasing system built in duodenum (duodenum built-in jejunum cannula releasing system) for backflow of food digested by stomach and a use method therefor.

BACKGROUND ART

Diabetes is a series of metabolic disturbance syndromes of sugar, protein, fat, water, electrolyte and so on, induced by pancreas islet dysfunction, insulin resistance and so on caused by various pathogenic factors, such as genetic factors, immune dysfunction, microbial infections and toxins thereof, which act on the body. Diabetes is classified into type I diabetes mellitus and type II diabetes mellitus, pregnancy diabetes and other special types of diabetes. Among diabetic patients, the type II diabetes mellitus occupies a proportion of about 95%.

In recent two decades, with global industrialization, and rapid pace of life, the prevalence of diabetes has risen sharply, and diabetes seriously affects people's quality of life and threatens health of human beings.

A main treatment method for type II diabetes mellitus (T2DM) in internal medicine department is a comprehensive regimen of diet control, exercise enhancement, oral medication, insulin treatment and so on, however, the above internal medical treatments cannot completely recover the blood glucose of the patient to be normal, nor can avoid the occurrence of complications of diabetes or further exacerbation of the disease.

Currently, a few hospitals in China and abroad are developing gastric bypass operation (GBP) for diabetes treatment and weight loss. The gastric bypass operation has proved therapeutic effect on the T2DM, but since surgery is to be performed, the trauma to the human body is relatively serious, and the wound is not easily healed after the surgery of the diabetic patient. Meanwhile, there is also a problem of high surgery expense, causing a heavy economic burden on the patient, and therefore, there are still some obstacles for popularization of the gastric bypass operation for treatment of diabetes.

At present, diabetes is also treated abroad by implanting a structure such as that similar to a gastric diverter in the gastrointestinal tract, for example, the stomach food fluid director disclosed in CN202751415U, wherein one end of a ball releasing line connects one end of a membrane tube and one end of a pushing tube with a membrane releasing ball, respectively, through a slipknot, the other end of the ball releasing line extends to the outside of the oral cavity, and by pulling the end of the ball releasing line located outside the oral cavity, the slipknot can be opened, such that the three, namely, the membrane tube, the pushing tube and the membrane releasing ball can be separated. With such a manner of fixing by a line, after releasing the membrane releasing ball, a relatively long section will quite likely enter a gap between the intestinal tract and the membrane tube, and under the extrusion of the intestinal tract, it is quite difficult for the ball releasing line to be disengaged from the membrane tube, and the membrane tube will be very easily re-pulled back when the ball releasing line is withdrawn, affecting the administration of surgery. Moreover, such a line-binding structure tends to cause the situation that the ball releasing line is mistakenly pulled to make the membrane releasing ball disengaged untimely.

SUMMARY

Technical Problem

An object of the present disclosure lies in providing a jejunum cannula releasing system built in duodenum which is simple in structure, convenient in operation, and easy to popularize, and a use method therefor.

Solution to the Problems

Technical Solution

In order to achieve the above object, the present disclosure discloses a jejunum cannula releasing system built in duodenum. The system includes an implanting device, a pushing assembly, a fixing line (30) and a releasing line (50), wherein the implanting device includes a storage tube shell (40), a releaser (10), a membrane tube (20) and a stent (60), the storage tube shell is tubular, the storage tube shell has a proximal opening and a distal opening, the membrane tube (20) and the stent (60) to be released are arranged in the storage tube shell (40) in a folded state, a proximal end of the membrane tube (20) is connected with a distal end of the stent (60), and the releaser (10) is provided at the distal opening of the storage tube shell (40) and connected with a distal end of the membrane tube (20); the pushing assembly includes a push-pull guidewire (74), an inner tube (73), a middle tube (72) and an outer tube (71) which are sleeved on one another from the inside out in sequence and are movable relatively with respect to each other, a distal end of the push-pull guidewire (74) abuts against the releaser (10); a part of the inner tube (73) is located inside the storage tube shell (40) and connected with the releaser (10); one end of the middle tube (72) protrudes into the storage tube shell (40) through the proximal opening of the storage tube shell (40), and this end of the middle tube is fixedly provided with a pushing block (41) located in the storage tube shell for pushing against the stent; the outer tube (71) is located outside the storage tube shell (40) and has one end directly or indirectly fixedly connected to the proximal opening of the storage tube shell; one end of the releasing line (50) is fixed on the inner tube (73), and the other end of the releasing line (50) is a free end; and one end of the fixing line (30) is fixed on the middle tube (72), and the other end of the fixing line (30) cooperates with the free end of the releasing line (50) to form a slipknot to connect the membrane tube (20) and the releaser (10).

In the present disclosure, the membrane tube and the releaser are connected through cooperation between the releasing line and the fixing line, one end of the releasing line is fixed on the inner tube, and the free end of the releasing line and the fixing line can be separated just by withdrawing the inner tube back with respect to the releaser, then the operation is simple, moreover, and as the connection is made jointly by the releasing line and the fixing line, when being withdrawn, the releasing line and the fixing line are threaded through the inner cavity of the membrane tube, the length of the releasing line and the fixing line in the gap between the intestinal tract and the membrane tube can be reduced as much as possible after the releaser is separated from the storage tube shell, avoiding pull-back of the membrane tube when withdrawing the releasing line and the fixing line. Furthermore, after the implanting device has been implanted, two ends of the above releasing line are both hidden from the operator, while the inner tube fixed with the releasing line may maintain a locked state and cannot be displaced with respect to the releaser, thus the releaser cannot be separated from the storage tube shell untimely due to the operator's mistake.

Preferably, the end of the fixing line connecting the membrane tube and the releaser is led out from a gap between the middle tube (72) and the inner tube. In this way, the occurrence of disengaging the free end of the fixing line from the releasing line before the releasing line is released can be reduced, and solidity of the line-binding structure is maintained.

Preferably, the fixing line led out from the gap between the middle tube and the inner tube is fixed on a pulling line knob (815). The fixing line can be conveniently withdrawn with the pulling line knob.

Preferably, the releaser (10) has an inner cavity, an outer circumferential wall of the releaser (10) is provided with one hole A (111) and at least two holes C (112) communicating with the inner cavity, one or more grooves A (113) are provided on a side wall of the releaser, the groove A (113) connects the hole A (111) and one of the holes C (112), for a wiring channel between the hole A (111) and the hole C (112), a groove B (114) is provided between adjacent holes C (112), and the groove B (114) is configured to connect a wiring channel between adjacent holes C (112); one end of the releasing line (50) is fixed to a distal end of the inner tube (73), and the other end of the releasing line (50) enters the inner cavity of the releaser and is led out from the hole A (111) at a top end of the releaser, and is wound on an outer sidewall of the releaser (10) in a circumferential distributed direction of the plurality of holes C (112) after passing through the groove A (113) and the groove B (114) in sequence; holes B (201), corresponding to the holes C (112), are provided on an outer circumferential wall at the distal end of the membrane tube (20), an end of the fixing line (30) penetrates through the inner cavity of the membrane tube (20), passes through the hole B (201) on the membrane tube and the hole C (112) on the releaser corresponding to the hole B, bypasses the releasing line and then passes through the hole C and the hole B to get back to the inner cavity of the membrane tube (20), then the above process is repeated until this end of the fixing line passes through the remaining holes B on the membrane tube and the corresponding holes C on the releaser in sequence.

Such line-binding structure is simple. When the releasing line is withdrawn, it is not easy for the releasing line to enter the gap between the intestinal tract and the membrane tube due to the relatively short length of the releasing line exposed from the releaser and its pull-back manner, and can be readily withdrawn, and after the releasing line is withdrawn, only several quite short coils of the fixing line are on the membrane tube, then even if extruded by the intestinal tract, it is instead easier for the fixing line to enter the inside of the membrane tube, so as to realize separation between the fixing line and the membrane tube, and the membrane tube will not be pulled back during the separation process of the fixing line. Moreover, by connecting the releaser and the membrane tube in a manner of multi-point fixation, the membrane tube can be stably driven to be unfolded, and the above cooperation manner between the releasing line and the fixing line further can quite easily realize the separation between the releasing ball and the membrane tube.

Preferably, the hole A (111) is located at the top of the releaser or provided close to the top of the releaser; and the plurality of holes C (112) are equidistantly distributed on the outer circumferential wall of the releaser centered on an installation axis of the releaser.

Preferably, in the pushing assembly, the proximal end of the middle tube (72) protrudes out from the proximal end of the outer tube (71), and the proximal end of the outer tube (71) is connected with a middle tube locking device (81) for locking or unlocking a position of the middle tube relative to the outer tube; the proximal end of the inner tube (73) protrudes out from the proximal end of the middle tube (72), and the proximal end of the middle tube (72) is connected with an inner tube locking device (82) for locking or unlocking a position of the inner tube relative to the middle tube; the proximal end of the push-pull guidewire (74) protrudes out from the proximal end of the inner tube, and a guidewire locking device (83) for locking or unlocking a position of the push-pull guidewire relative to the inner tube is connected to the proximal end of the inner tube.

By providing the above middle tube locking device, the inner tube locking device and the guidewire locking device, it facilitates the pushing assembly in manipulating the pushing process in an orderly manner.

Preferably, the middle tube locking device (81), the inner tube locking device (82) and the guidewire locking device (83) are in the same structure for realizing locking or unlocking, including a housing (811), an end of the housing is fixed in a contracted manner to the proximal end of the outer tube, the middle tube or the inner tube, the housing has a channel from a proximal opening thereof to a distal opening thereof, the housing is provided thereon with an adjustment knob (812), the adjustment knob has an extension end (8121), the channel is provided therein with a sealing ring (813) which can be pressed by an extension end (8121) of the adjustment knob, so as to tightly compress the middle tube (72), the inner tube (73) or the push-pull guidewire (74) passing through the channel.

As the sealing ring per se is elastic, the tightness between the sealing ring and the push-pull guidewire, the inner tube or the middle tube in the corresponding pushing assembly can be controlled and adjusted with the adjustment knob, and whether tight locking is achieved is controlled by adjusting the frictional force.

Preferably, an inner wall of the housing (811) is formed with a limiting step (8111) for restricting the position of the sealing ring inside the housing. By providing the limiting step, the sealing ring is allowed to be always corresponding to the extension end of the adjustment knob.

Preferably, the guidewire locking device (83) includes a luer taper (84) in communication with the inner tube, configured to control whether the adjustment knob of the push-pull guidewire can be pushed to be detachably connected on the luer taper, and the adjustment knob is provided with a channel for the push-pull guidewire to pass through. With such configuration, normal saline can be injected into the inner tube through the luer taper, thus accelerating the unfolding of the membrane tube.

Preferably, the releaser (10) has an outer circumferential wall (11) and an inner cavity (12) capable of communicating with the inside of the storage tube shell, the releaser is provided thereon with a guidewire quick exchange channel (116), the guidewire quick exchange channel (116) is formed by direct communication of two channel openings (1161) on the releaser, and the two channel openings are both located on an outer surface of the outer circumferential wall exposed to the storage tube shell.

By providing the guidewire quick exchange channel, connection with the implanting device can be conveniently formed so as to guide the implanting device to enter a predetermined position in earlier stage, moreover, after the releaser and the storage tube shell are separated, the releaser can be continuously allowed to go deeper along the guidewire into the depth of intestinal tract, so as to complete the surgery quickly, reduce the operation difficulty for the operator, and also reduce the patient's pain.

Preferably, the guidewire quick exchange channel does not pass through the inner cavity of the releaser, thus keeping off the pushing assembly.

Preferably, the releaser (10) is provided thereon with a guidewire groove (115) cooperating with the push-pull guidewire in a manner of insertion, which can prevent the push-pull guidewire from being separated from the releaser and scratching the intestinal tract in the process of withdrawing the inner tube to drive the releasing line to be released, ensuring safety of the surgery.

Preferably, the releaser contains a developing material which can be developed under X-ray. The developing material facilitates observing the position of the releaser in the human body during the surgery. In this way, the position of the releaser can be precisely shown under the X-ray, so as to observe whether the releaser is discharged out from the body after the surgery is completed.

The present disclosure further discloses a method for using the jejunum cannula releasing system built in duodenum. The method includes following steps:
1) guiding the implanting device into duodenum through the guidewire;
2) operating the middle tube (72) to enable the middle tube to drive the pushing block (41) to move away from an operator, so as to disengage the releaser (10) and the storage tube shell (40) while no displacement occurs between the inner tube (73) and the releaser (10);
3) operating the inner tube (73) to enable the inner tube to push the releaser (10) to move away from an operator, so as to unfold the membrane tube (20);
4) maintaining a position of the releaser (10) by the push-pull guidewire (74), operating the inner tube (73) to move towards the operator, wherein the inner tube drives the free end of the releasing line (50) to be separated from the fixing line (30), so that the slipknot connecting the membrane tube (20), the releaser (10) and the inner tube (73) is unknotted; and
5) operating the middle tube (72) and/or the outer tube (71) to enable the stent (60) to be separated from the storage tube shell (40) to enter a predetermined position in the intestinal tract.

Preferably, in step 2), unlocking a position of the middle tube (72) with respect to the outer tube (71), so that the middle tube (72) is movable relative to the outer tube (71), and maintaining synchronous movement among the inner tube (73), the middle tube (72) and the push-pull guidewire (74); in step 3), unlocking a position of the inner tube (73) with respect to the middle tube (72), so that the inner tube (73) is movable relative to the middle tube (72), and maintaining synchronous movement between the push-pull guidewire (74) and the inner tube (73).

Preferably, before the stent is separated from the storage tube shell, injecting normal saline into the inner tube to help to unfold the membrane tube.

The above method for using the jejunum cannula releasing system built in duodenum is quite simple in operation, and is easy to popularize, and the therapeutic effect of gastric bypass operation can be achieved without surgery on the patient, then the patient's pains can be reduced, and meanwhile the treatment cost is also saved for the patients.

BENEFICIAL EFFECTS OF DISCLOSURE

Beneficial Effects

The above jejunum cannula releasing system built in duodenum has following beneficial effects:
(1) the inner tube, the membrane tube and the releaser are connected through cooperation between the releasing line and the fixing line, the free end of the releasing line and the fixing line can be separated just by withdrawing the inner tube back with respect to the releaser, then the operation is simple, moreover, and as the connection is made jointly by the releasing line and the fixing line, the length of the releasing line and the fixing line in the gap between the intestinal tract and the membrane tube can be reduced as much as possible after the releaser is separated from the storage tube shell, avoiding pull-back of the membrane tube when withdrawing the releasing line and the fixing line.
(2) after the implanting device has been implanted, two ends of the above releasing line are both hidden from the operator, while the inner tube fixed with the releasing line may maintain a locked state and cannot be displaced with respect to the releaser, thus the releaser cannot be separated from the storage tube shell untimely due to the operator's mistake.

In the drawings, 10. releaser, 11. outer circumferential wall, 111. hole A, 112. hole C, 113. groove A, 114. groove B, 115. guidewire groove, 116. guidewire quick exchange channel, 1161. channel opening, 1162. guidewire for quick exchange, 12. inner cavity, 20. membrane tube, 201. hole B, 30. fixing line, 40. storage tube shell, 401. connecting sleeve, 41. pushing block, 50. releasing line, 60. stent, 71. outer tube, 72. middle tube, 73. inner tube, 74. push-pull guidewire, 81. middle tube locking device, 811. housing, 8111. limiting step, 812. adjustment knob, 8121. extension end, 813. sealing ring, 814. heat-shrinkable sleeve, 815. pulling line knob, 82. inner tube locking device, 83. guidewire locking device, 84. luer taper.

DETAILED DESCRIPTION OF EMBODIMENTS

Embodiments of the present disclosure are described in detail below in combination with accompanying drawings. Therein, an end close to an operator is a proximal end, an end away from the operator is a distal end, a direction from the proximal end towards the distal end is a front end, and vice versa is a proximal end.

Figure 1:
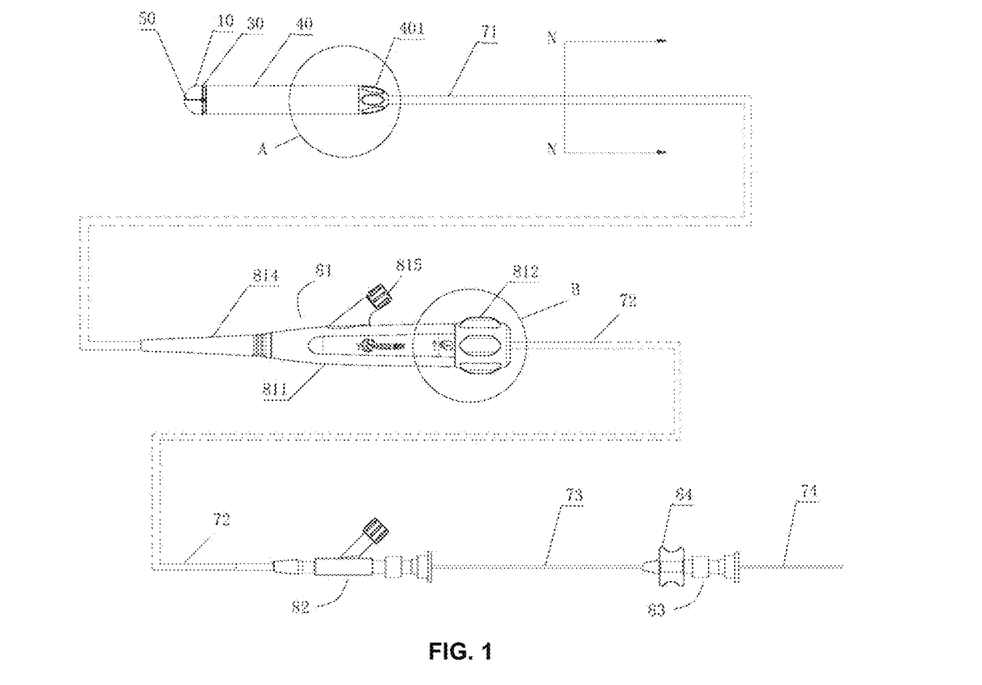
FIG. 1 is a structural schematic view of the present disclosure.
Figure 2:
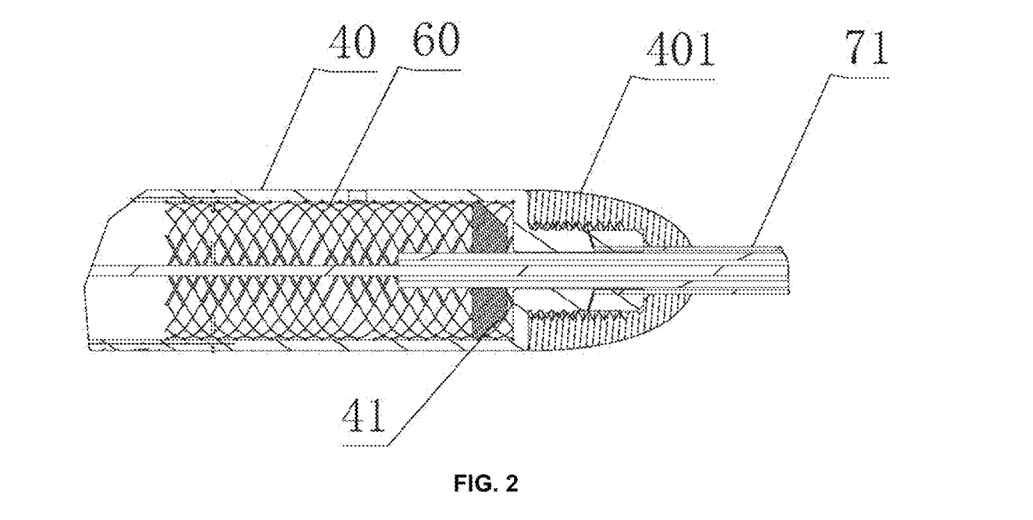
FIG. 2 is a sectional view of A in FIG. 1.
Figure 3:
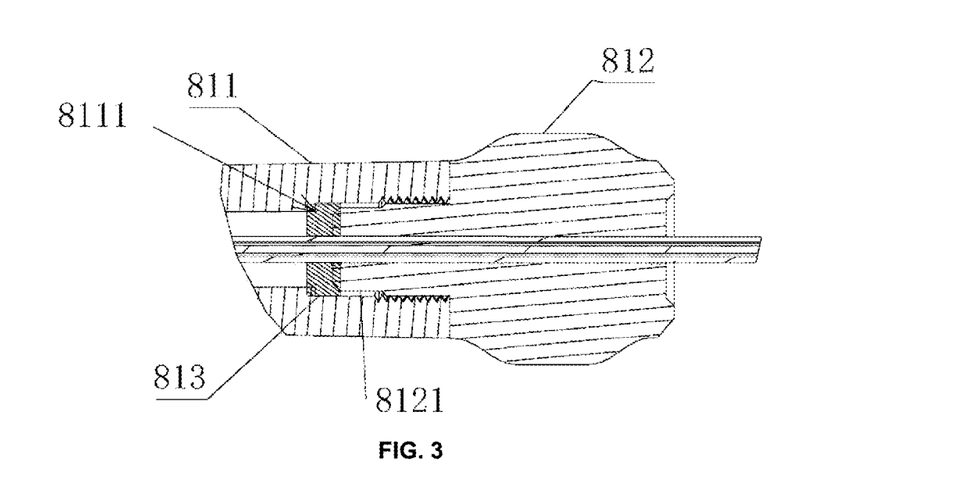
FIG. 3 is a sectional view of B in FIG. 1.
Figure 4:
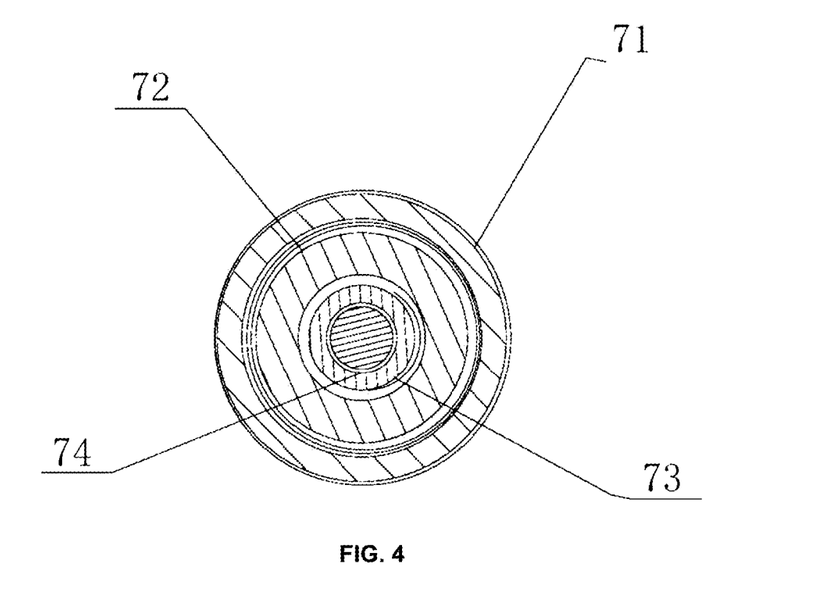
FIG. 4 is a cross-section view along N-N in FIG. 1.

A jejunum cannula releasing system built in duodenum as shown in FIGS. 1-3 includes an implanting device, a pushing assembly, a fixing line 30 and a releasing line 50.

The implanting device is used in the human body, and is implanted to duodenum of the human body close to stomach pylorus and/or an upper part of the stomach pylorus via oral cavity of the human body through the gastroscope. The implanting device includes a storage tube shell 40, a releaser 10, a membrane tube 20 and a stent 60, wherein the storage tube shell 40 is tubular, the storage tube shell 40 has a proximal opening and a distal opening, the membrane tube 20 and the stent 60 to be released are arranged in the storage tube shell 40 in a folded state, and a proximal end of the membrane tube 20 is connected with a distal end of the stent 60.

Figure 5:
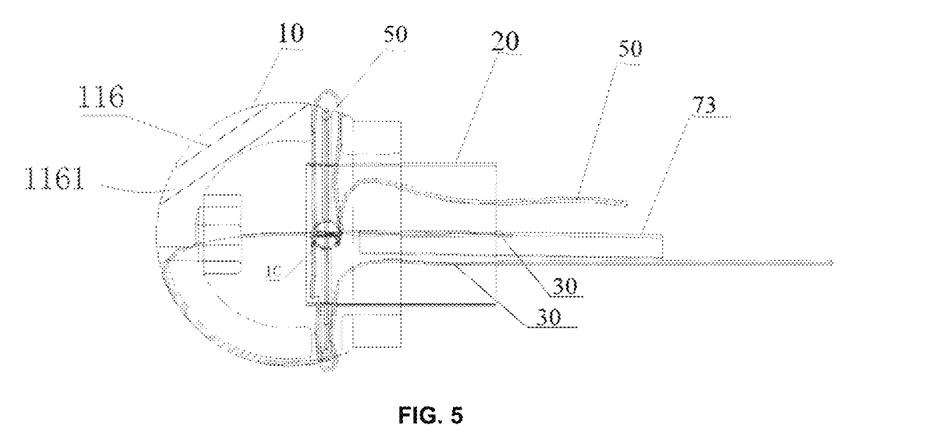
FIG. 5 is a first schematic view of a fixing structure of a membrane tube and a releasing ball.
Figure 6:
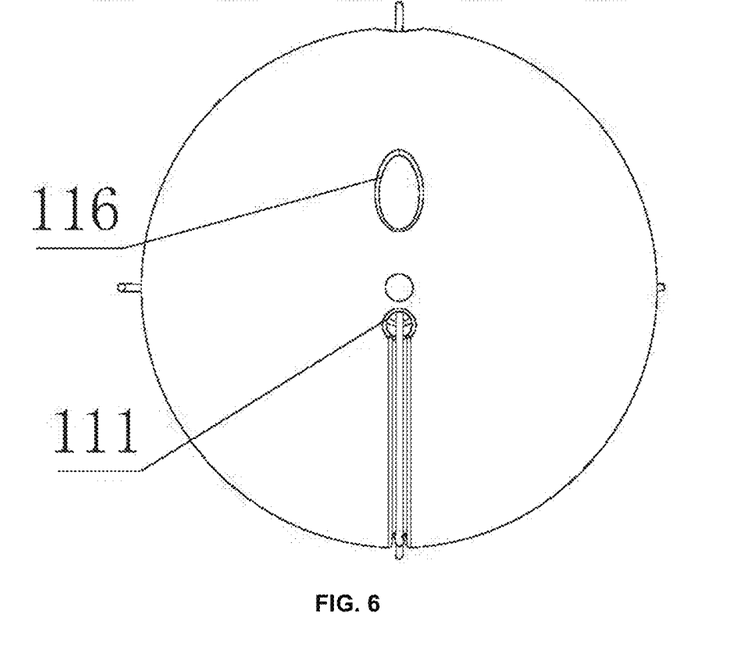
FIG. 6 is a structural schematic view of top of the releasing ball.
Figure 7:
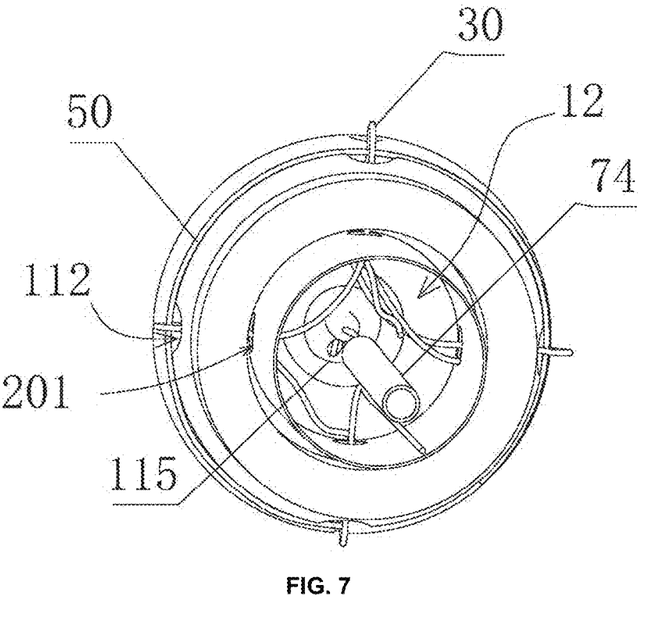
FIG. 7 is a second schematic view of the fixing structure of the membrane tube and the releasing ball.
Figure 8:
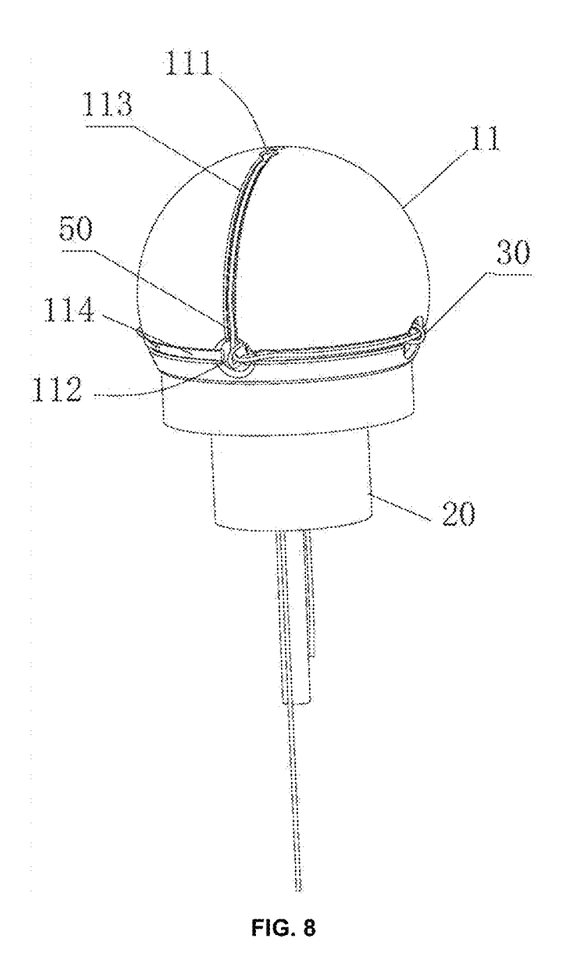
FIG. 8 is a schematic view of a line-binding structure of a releasing line and a fixing line on the releasing ball.
Figure 9:
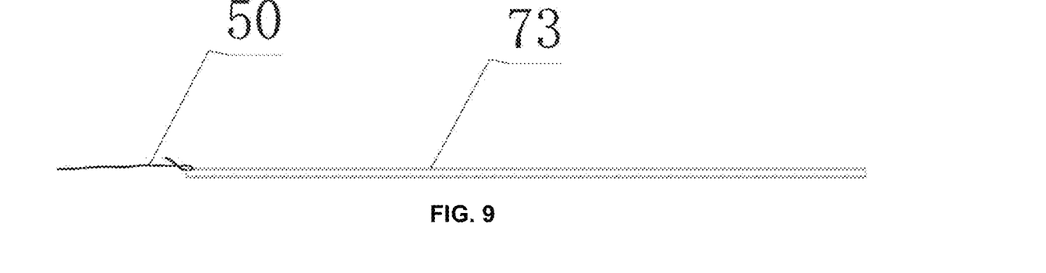
FIG. 9 is a schematic view of a connection structure of an inner tube and the releasing line.
Figure 10:
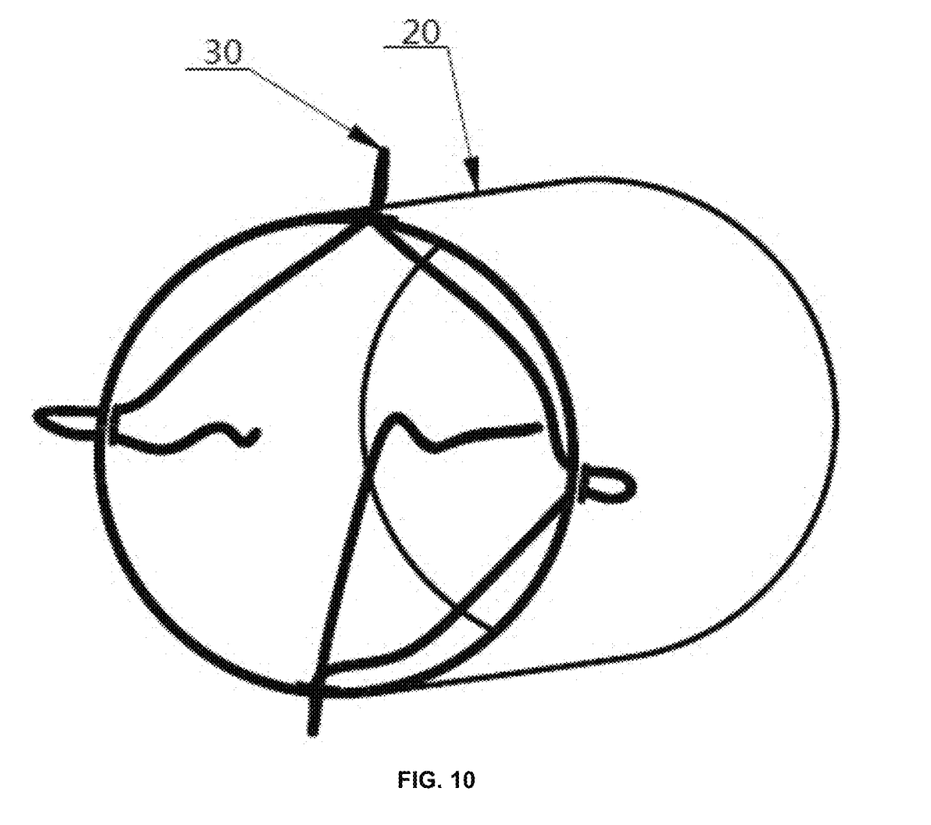
FIG. 10 is a schematic view of a connection structure of the fixing line and the membrane tube.

The releaser 10 is provided at the distal opening of the storage tube shell 40 and connected with a distal end of the membrane tube 20, and the releaser 10 is made of a material capable of being digested, absorbed or dissolved by the intestinal tract of the human body. The releaser 10 has an outer circumferential wall 11 and an inner cavity 12 capable of communicating with the inside of the storage tube shell. The outer circumferential wall of the releaser is provided with one hole A 111 and at least two holes C 112 communicating with the inner cavity. The hole A 111 is located at the top of the releaser 10 or provided close to the top of the releaser. The top refers to a most distal end of the releaser in the direction away from an operator on its axis. The plurality of holes C 112 are equidistantly distributed on an outer circumferential surface of the releaser centered on the axis of the releaser 10. One or more grooves A 113 are provided on a side wall of the releaser. The groove A 113 connects the hole A 111 and one of the holes C 112, for a wiring channel between the hole A 111 and the hole C 112. A groove B 114 is provided between adjacent holes C 112, and the groove B 114 is configured to connect a wiring channel between adjacent holes C 112; the outer circumferential wall is substantial in a spherical or hemispherical arc structure, thus preventing the releaser from scratching the intestinal tract.

The releaser 10 and the distal end of the membrane tube 20 are connected through the releasing line 50 and the fixing line 30, and holes B 201, corresponding to the holes C 112, are provided on the outer circumferential wall at the distal end of the membrane tube 20.

As shown in FIG. 1, FIG. 2, FIG. 4 and FIGS. 8-10, the pushing assembly includes a push-pull guidewire 74, an inner tube 73, a middle tube 72 and an outer tube 71 which are sleeved on one another from the inside out in sequence and can move relatively with respect to each other. A distal end of the push-pull guidewire 74 abuts against the releaser 10; a part of the inner tube 73 is located inside the storage tube shell 40 and connected with the releaser 10; one end of the releasing line 50 is fixed to a distal end of the inner tube 73, and the other end of the releasing line 50 enters the inner cavity of the releaser 10 and is led out from the hole A 111 at a top end of the releaser, and is wound on an outer sidewall of the releaser 10 in a circumferential distributed direction of the hole C 112 after passing through the groove A 113 and the groove B 114 in sequence. One end of the fixing line 30 is fixed on the middle tube, and generally fixed to a distal end of the middle tube, the other end of the fixing line is a free end, and this free end penetrates through the inner cavity of the membrane tube 20, passes through the hole B 201 on the membrane tube 20 and the hole C 112 on the releaser 10 corresponding to the hole B, bypasses the releasing line 50 and then passes through the hole C 112 and the hole B 201 to get back to the inner cavity of the membrane tube 20. Then the above process is repeated until this end of the fixing line passes through the remaining holes B 201 on the membrane tube and the corresponding holes C 112 on the releaser in sequence. The releaser and the membrane tube are connected through cooperation between the fixing line 30 and the releasing line, and after the releasing line is released, only a few very small coils of the fixing line 30 are exposed from the hole C, in this way, when the fixing line is withdrawn, the fixing line runs through the inner cavity of the membrane tube, and will not be brought back to the membrane tube. Further, as the line head of the free end is suspended without any connection structure after the free end of the fixing line 30 connects the hole C and the hole B in pairs in the form of coil, a part of coils having been connected in the holes C and the holes B may be disengaged, then on one hand, the stability of the connection structure between the releaser 10 and the membrane tube 20 will be affected, and on the other hand, a relatively long line head may enter between the membrane tube and the intestinal body, thus, the membrane tube may be brought back together when the fixing line is pulled back, therefore, the free end of the fixing line is preferably led out from the gap between the middle tube 72 and the inner tube, in this way, it can be ensured that the fixing line 30 is completely withdrawn from the inner cavity of the membrane tube 20 when the fixing line is withdrawn. And preferably, this free end is fixed on a pulling line knob 815, so as to facilitate pulling back the fixing line 30.

One end of the middle tube 72 protrudes into the storage tube shell 40 through the proximal opening of the storage tube shell, and this end of the middle tube is fixedly provided with a pushing block located in the storage tube shell for pushing against the stent 60. Specifically, the pushing block 41 abuts against a proximal end of the stent 60, a distal end of the stent 60 is connected with a proximal end of the membrane tube 20, and the pushing block 41 pushes the stent 60 to move together with the membrane tube 20. The outer tube 71 is located outside the storage tube shell 40, and has one end directly or indirectly fixedly connected to the proximal opening of the storage tube shell 40; in the present embodiment, the outer tube 71 is fixed on the storage tube shell 40 through a connecting sleeve 401 connected at the proximal opening of the storage tube shell 40 and communicates with the inner cavity of the storage tube shell, and the storage tube shell 40 and the connecting sleeve 401 are in threaded connection.

In the pushing assembly, the proximal end of the middle tube 72 protrudes out from the proximal end of the outer tube 71, and the proximal end of the outer tube 71 is connected with a middle tube locking device 81 for locking or unlocking a position of the middle tube relative to the outer tube; the proximal end of the inner tube 73 protrudes out from the proximal end of the middle tube 72, and the proximal end of the middle tube 72 is connected with an inner tube locking device 82 for locking or unlocking a position of the inner tube relative to the middle tube; the proximal end of a push-pull guidewire 74 protrudes out from the proximal end of the inner tube, and a guidewire locking device 83 for locking or unlocking a position of the push-pull guidewire relative to the inner tube is connected to the proximal end of the inner tube. A middle tube locking device 81, an inner tube locking device 82 and the guidewire locking device 83 may adopt the same structure to achieve the function of locking or unlocking. This structure includes a housing 811. An end of the housing is fixed in a contracted manner to the proximal end of the outer tube, the middle tube or the inner tube. The housing has a channel from a proximal opening thereof to a distal opening thereof. The housing is provided thereon with an adjustment knob 812. The adjustment knob has an extension end 8121. The channel is provided therein with a sealing ring 813 which can be pressed by an extension end 8121 of the adjustment knob, so as to tightly compress the middle tube 72, the inner tube 73 or the push-pull guidewire 74 passing through the channel. In the above, the sealing ring of the middle tube locking device 81 is sheathed on the outer periphery of the middle tube, the sealing ring of the inner tube locking device 82 is sheathed on the outer periphery of the inner tube, and the sealing ring of the guidewire locking device 83 is sheathed on the outer periphery of the push-pull guidewire. An inner wall of the housing 811 is formed with a limiting step 8111 for restricting the position of the sealing ring inside the housing, so that it can be ensured that during the process of pressing the sealing ring 813 with the extension end 8121 of the adjustment knob, the sealing ring 813 is always aligned with the extension end 8121, so that the sealing ring is pressed to increase a frictional force with the middle tube, the inner tube or the push-pull guidewire, thereby achieving locking; on the contrary, reducing the pressure between the adjustment knob and the sealing ring may decrease the frictional force between the sealing ring and the middle tube, the inner tube or the push-pull guidewire, thereby achieving unlocking.

In the present embodiment, the distal ends of the inner tube locking device, the inner tube locking device and/or the guidewire locking device are connected with the outer tube 71, the middle tube 72 and/or the inner tube 73 through a heat-shrinkable sleeve 814, so as to facilitate the assembling between the above locking devices and pushing tubes such as the inner tube, the middle tube and the outer tube in the pushing assembly.

Preferably, the pulling line knob 815 is provided on the housing of the middle tube locking device 81 or the inner tube locking device 82.

A method for using the above jejunum cannula releasing system built in duodenum includes following steps:
1. introducing the guidewire into the intestinal tract of the human body through a through the scope TTS, and then withdrawing the endoscope while keeping the guidewire in place;
2. guiding the implanting device into the duodenum through the guidewire;
3. unlocking the middle tube locking device 81 to push the middle tube 72, so that the middle tube 72 drives the pushing block 41 to advance, at which time the inner tube 73 and the push-pull guidewire 74 are pushed forward in the locking condition by the inner tube locking device 82 and the guidewire locking device 83, so that the releaser 10 is disengaged from the storage tube shell 40, and as the inner tube 73 is not displaced with the releaser 10, the releasing line 50 will not be easily disengaged from the releaser;
4. continuously pushing the middle tube 72 until the releaser 10 and the membrane tube 20 enter the intestinal tract while the stent 60 is still located inside the storage tube shell, then stopping pushing the middle tube 72, wherein this step is prepared for unfolding of the membrane tube 20 in the intestinal tract;
5. unlocking the inner tube locking device 82, and pushing the inner tube 73, so that the releaser 10 is advanced to drive the membrane tube 20 to unfold, at which time the push-pull guidewire 74 is pushed forward due to the locking condition of the guidewire locking device 83, wherein in this step, after the inner tube 73 is pushed until the releaser 10 cannot be pushed continuously, the pushing of the inner tube 73 is stopped, and at this time, it indicates that the membrane tube 20 has been fully unfolded in a length direction thereof;
6. unlocking the guidewire locking device 83, so that the inner tube 73 and the push-pull guidewire 74 can move with respect to each other, abutting against the releaser 10 with the push-pull guidewire 74, and slowly withdrawing the inner tube 73 backward while the releaser 10 will not return with the inner tube 73, so that the releasing line 50 can be disengaged from the releaser 10;
7. operating the pulling line knob 815 to pull the fixing line 30 to completely enter the middle tube 72, at which time the releaser 10 is separated from the membrane tube 20, wherein the fixing line 30 passes through a gap between the middle tube 72 and the inner tube 73;
8. withdrawing the push-pull guidewire 74;
9. pushing the middle tube 72 to advance so that the pushing block 41 pushes the stent 60, or holding a position of the stent 60 by the pushing block 41 at the distal end of the middle tube 72, and meanwhile pulling the outer tube 71 backward, so that the stent 60 is separated from the storage tube shell 40; and
10. withdrawing the inner tube 73, the middle tube 72 and the outer tube 71.

Preferably, in the above jejunum cannula releasing system built in duodenum, the middle tube locking device 81, the inner tube locking device 82 and the guidewire locking device 83 can adopt the same structure or different structures, as long as the above functions of locking and unlocking can be achieved. In the above, the guidewire locking device 83 may include a luer taper 84 in communication with the inner tube, configured to control whether the adjustment knob of the push-pull guidewire can be pushed to be detachably connected on the luer taper, and the adjustment knob is provided with a channel for the push-pull guidewire to pass through. In this way, in the use method for the above releasing system, before the stent 60 is disengaged from the storage tube shell 40, the push-pull guidewire can be withdrawn first, the adjustment knob on the guidewire locking device is dismounted, and then normal saline is injected into the inner tube 73 through the luer taper on the guidewire locking device, thereby helping to unfold the membrane tube 20 as much as possible.

Preferably, the releaser 10 contains a developing material, for example, barium sulfate, bismuth carbonate, tungsten or the like, which can be developed under X-ray, and can accurately show the position of the releaser under X-ray, so as to facilitate observing whether the releaser is discharged to the outside of the body after the surgery is completed. The developing material may be directly used as a part of raw materials for processing the releaser, or may be coated on a surface of the releaser, or may be provided as a developing mark adhered to the releaser by medical glue. Furthermore, the storage tube shell 40 may be made of a transparent material, in this way the operator can observe the positions of the stent 60 and the pushing block 41 located inside the storage tube shell in real time, facilitating in more intuitively determining a stop position of the pushing block when the middle tube is manipulated to push the pushing block.

In the present embodiment, as the push-pull guidewire needs to press against the releaser, in the process of withdrawing the inner tube to drive the releasing line to be released, so as to limit the position of the releaser, in order to prevent the push-pull guidewire from falling off the releaser and scratching the intestinal tract in this process, the releaser 10 is provided thereon with a guidewire groove 115 cooperating with the push-pull guidewire in a manner of insertion, and the distal end of the push-pull guidewire 74 is inserted in this guidewire groove 115.

Figure 11:
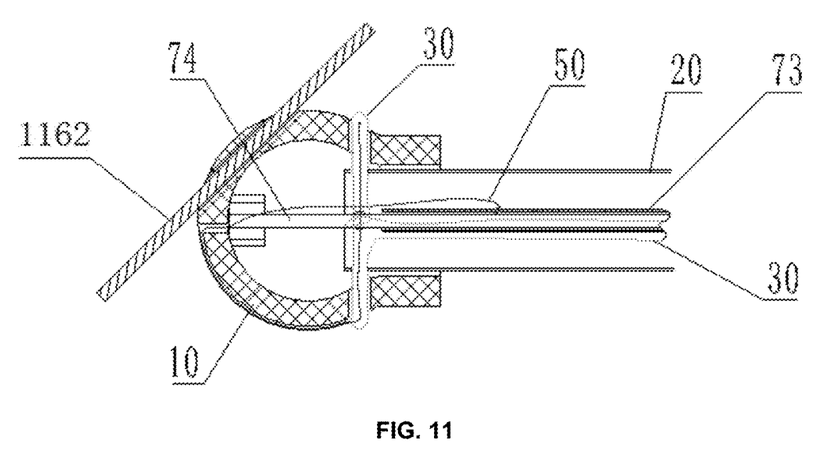
FIG. 11 is a schematic view showing the guidewire.

In the above step 2, the structure for the guidewire to guide the implanting device to enter the duodenum is as follows: the releaser is provided thereon with a hole communicating with the inner cavity of the releaser, wherein the hole is located on a central axis of the releaser, the guidewire is in sequence threaded into the inner cavity of the releaser from this hole, then enters the inner tube from the distal end of the inner tube, and then penetrates out from the proximal end of the inner tube, so as to guide the implanting device to enter a predetermined position by the guidewire. Such structure costs a relatively long time of operation. In view of this problem, in the present disclosure, the releaser 10 is provided thereon with a guidewire quick exchange channel 116 used for allowing a guidewire 1162 for quick exchange to pass therethrough. The guidewire quick exchange channel 116 is formed by linear communication of two channel openings 1161 on the releaser, and the two channel openings are both located on an outer surface of the outer circumferential wall exposed to the storage tube shell, and the guidewire quick exchange channel does not pass through the inner cavity of the releaser, so as to be capable of keeping off the pushing assembly extending into the inner cavity. In the present embodiment, the guidewire quick exchange channel 116 is arranged obliquely, and preferably, the guidewire quick exchange channel 116 has a certain angle with the central axis of the releaser 10. By providing the guidewire quick exchange channel 116, connection can be conveniently formed with the implanting device, so as to guide the implanting device to enter a predetermined position in earlier stage, moreover, after the releaser 10 and the storage tube shell 40 are disengaged, the releaser can be continuously allowed to go deeper along the guidewire into the depth of intestinal tract, so as to complete the surgery quickly, reduce the operation difficulty of the operator, and also reduce the patient's pain.

What is claimed is:

1. A jejunum cannula releasing system configured to be built in duodenum, comprising an implanting device, a pushing assembly, a fixing line and a releasing line, wherein the implanting device comprises a storage tube shell, a releaser, a membrane tube and a stent, wherein the storage tube shell is tubular, the storage tube shell has a proximal opening and a distal opening, the membrane tube and the stent to be released are arranged in the storage tube shell in a folded state, a proximal end of the membrane tube is connected with a distal end of the stent, and the releaser is provided at the distal opening of the storage tube shell and connected with a distal end of the membrane tube; the pushing assembly comprises a push-pull guidewire, an inner tube, a middle tube and an outer tube, which are sleeved on one another from the inside out in sequence and are movable relatively with respect to each other, wherein a distal end of the push-pull guidewire abuts against the releaser; a part of the inner tube is located inside the storage tube shell and connected with the releaser;

one end of the middle tube protrudes into the storage tube shell through the proximal opening of the storage tube shell, and the one end of the middle tube is fixedly provided with a pushing block located in the storage tube shell for pushing against the stent; the outer tube is located outside the storage tube shell and has one end directly or indirectly fixedly connected to the proximal opening of the storage tube shell; one end of the releasing line is fixed on the inner tube, and the other end of the releasing line is a free end; and one end of the fixing line is fixed on the middle tube, and the other end of the fixing line cooperates with the free end of the releasing line to form a slipknot to connect the membrane tube and the releaser, wherein the releaser has an inner cavity, an outer circumferential wall of the releaser is provided with one hole A and at least two holes C communicating with the inner cavity, one or more grooves A are provided on a side wall of the releaser, each of the grooves A connects the hole A and one of the holes C and is used as a wiring channel between the hole A and the one of the holes C, a groove B is provided between adjacent holes C, and the groove B is configured to connect a wiring channel between adjacent holes C; the releasing line is fixed to a distal end of the inner tube, and the free end of the releasing line enters the inner cavity of the releaser and is led out from the hole A at a top end of the releaser, and is wound on the outer circumferential wall of the releaser in a circumferential distributed direction of a plurality of the holes C after passing through one of the one or more grooves A and the groove B in sequence; holes B, corresponding to the holes C, are provided on an outer circumferential wall at the distal end of the membrane tube, the other end of the fixing line penetrates through an inner cavity of the membrane tube, passes through one of the holes B on the membrane tube and one of the holes C on the releaser corresponding to the one of the holes B, bypasses the releasing line and then passes through the one of the holes C and the one of the holes B to get back to the inner cavity of the membrane tube, then said process is repeated until this end of the fixing line passes through remaining holes B on the membrane tube and corresponding holes C on the releaser in sequence.

2. The jejunum cannula releasing system configured to be built in duodenum according to claim 1, wherein the other end of the fixing line connecting the membrane tube and the releaser is led out from a gap between the middle tube and the inner tube.

3. The jejunum cannula releasing system configured to be built in duodenum according to claim 2, wherein the fixing line led out from the gap between the middle tube and the inner tube is fixed on a pulling line knob.

4. The jejunum cannula releasing system configured to be built in duodenum according to claim 1, wherein a plurality of the holes C are equidistantly distributed on the outer circumferential wall of the releaser centered on an installation axis of the releaser.

5. The jejunum cannula releasing system configured to be built in duodenum according to claim 1, wherein in the pushing assembly, a proximal end of the middle tube protrudes out from a proximal end of the outer tube, and the proximal end of the outer tube is connected with a middle tube locking device for locking or unlocking a position of the middle tube relative to the outer tube; a proximal end of the inner tube protrudes out from the proximal end of the middle tube, and the proximal end of the middle tube is connected with an inner tube locking device for locking or unlocking a position of the inner tube relative to the middle tube; a proximal end of the push-pull guidewire protrudes out from the proximal end of the inner tube, and the proximal end of the inner tube is connected with a guidewire locking device for locking or unlocking a position of the push-pull guidewire relative to the inner tube.

6. The jejunum cannula releasing system configured to be built in duodenum according to claim 5, wherein the middle tube locking device, the inner tube locking device and the guidewire locking device realize locking or unlocking using a same structure, comprising a housing, wherein an end of the housing is fixed in a contracted manner to the proximal end of the outer tube, the middle tube or the inner tube, the housing has a channel from a proximal opening thereof to a distal opening thereof, the housing is provided thereon with an adjustment knob, the adjustment knob has an extension end, the channel is provided therein with a sealing ring which is able to be pressed by the extension end of the adjustment knob, so as to tightly compress the middle tube, the inner tube or the push-pull guidewire passing through the channel; an inner wall of the housing is provided with a limiting step for restricting a position of the sealing ring inside the housing; and the guidewire locking device comprises a luer taper in communication with the inner tube, which is configured to control whether the adjustment knob of the push-pull guidewire is capable of being pushed to be detachably connected on the luer taper, and the adjustment knob is provided with a channel for the push-pull guidewire to pass through.

7. The jejunum cannula releasing system configured to be built in duodenum according to claim 1, wherein the inner cavity of the releaser is capable of communicating with an inside of the storage tube shell, the releaser is provided thereon with a guidewire quick exchange channel, wherein the guidewire quick exchange channel is formed by direct communication of two channel openings on the releaser, and the two channel openings are both located on the outer circumferential wall of the releaser, the guidewire quick exchange channel does not pass through the inner cavity of the releaser; the releaser is provided thereon with a guidewire groove cooperating with the push-pull guidewire in a manner of insertion; and the releaser contains a developing material which is able to be developed under X-ray.

8. A method for using the jejunum cannula releasing system configured to be built in duodenum according to claim 1, comprising following steps:
1) guiding the implanting device into duodenum through a guidewire;
2) operating the middle tube to enable the middle tube to drive the pushing block to move away from an operator, so as to disengage the releaser and the storage tube shell while no displacement occurs between the inner tube and the releaser;
3) operating the inner tube to enable the inner tube to push the releaser to move away from the operator so as to unfold the membrane tube;
4) maintaining a position of the releaser by the push-pull guidewire, operating the inner tube to move towards the operator, wherein the inner tube drives the free end of the releasing line to be separated from the fixing line, so that the slipknot connecting the membrane tube, the releaser and the inner tube is unknotted; and
5) operating the middle tube and/or the outer tube to enable the stent to be separated from the storage tube shell and enter a predetermined position in an intestinal tract.

9. The method for using the jejunum cannula releasing system configured to be built in duodenum according to claim 8, wherein in step 2), a position of the middle tube with respect to the outer tube is unlocked, so that the middle tube is movable relative to the outer tube, and synchronous movement among the inner tube, the middle tube and the push-pull guidewire is maintained; in step 3), a position of the inner tube with respect to the middle tube is unlocked, so that the inner tube is movable relative to the middle tube, and synchronous movement between the push-pull guidewire and the inner tube is maintained; and before the stent is separated from the storage tube shell, normal saline is injected into the inner tube to help to unfold the membrane tube.

10. The method for using the jejunum cannula releasing system configured to be built in duodenum according to claim 8, wherein the other end of the fixing line connecting the membrane tube and the releaser is led out from a gap between the middle tube and the inner tube.

11. The method for using the jejunum cannula releasing system configured to be built in duodenum according to claim 10, wherein the end of the fixing line led out from the gap between the middle tube and the inner tube is fixed on a pulling line knob.

12. The method for using the jejunum cannula releasing system configured to be built in duodenum according to claim 8, wherein a plurality of the holes C are equidistantly distributed on the outer circumferential wall of the releaser centered on an installation axis of the releaser.

13. The method for using the jejunum cannula releasing system configured to be built in duodenum according to claim 8, wherein in the pushing assembly, a proximal end of the middle tube protrudes out from a proximal end of the outer tube, and the proximal end of the outer tube is connected with a middle tube locking device for locking or unlocking a position of the middle tube relative to the outer tube; a proximal end of the inner tube protrudes out from the proximal end of the middle tube, and the proximal end of the middle tube is connected with an inner tube locking device for locking or unlocking a position of the inner tube relative to the middle tube; a proximal end of the push-pull guidewire protrudes out from the proximal end of the inner tube, and the proximal end of the inner tube is connected with a guidewire locking device for locking or unlocking a position of the push-pull guidewire relative to the inner tube.

14. The method for using the jejunum cannula releasing system configured to be built in duodenum according to claim 13, wherein the middle tube locking device, the inner tube locking device and the guidewire locking device realize locking or unlocking using a same structure, comprising a housing, wherein an end of the housing is fixed in a contracted manner to the proximal end of the outer tube, the middle tube or the inner tube, the housing has a channel from a proximal opening thereof to a distal opening thereof, the housing is provided thereon with an adjustment knob, the adjustment knob has an extension end, the channel is provided therein with a sealing ring which is able to be pressed by the extension end of the adjustment knob, so as to tightly compress the middle tube, the inner tube or the push-pull guidewire passing through the channel; an inner wall of the housing is provided with a limiting step for restricting a position of the sealing ring inside the housing;

and the guidewire locking device comprises a luer taper in communication with the inner tube, which is configured to control whether the adjustment knob of the push-pull guidewire is capable of being pushed to be detachably connected on the luer taper, and the adjustment knob is provided with a channel for the push-pull guidewire to pass through.

15. The method for using the jejunum cannula releasing system configured to be built in duodenum according to claim 8, wherein the inner cavity of the releaser is capable of communicating with an inside of the storage tube shell, the releaser is provided thereon with a guidewire quick exchange channel, wherein the guidewire quick exchange channel is formed by direct communication of two channel openings on the releaser, and the two channel openings are both located on the outer circumferential wall of the releaser, the guidewire quick exchange channel does not pass through the inner cavity of the releaser; the releaser is provided thereon with a guidewire groove cooperating with the push-pull guidewire in a manner of insertion; and the releaser contains a developing material which is able to be developed under X-ray.

* * * * *